United States Patent [19]
Beckman et al.

[11] Patent Number: 5,325,865
[45] Date of Patent: Jul. 5, 1994

[54] INTRACRANIAL PRESSURE MONITORING SYSTEM

[75] Inventors: Ronald B. Beckman, Mission Viejo; Jesse N. Bequette, Costa Mesa, both of Calif.

[73] Assignee: Baxter International, Inc., Deerfield, Ill.

[21] Appl. No.: 485,349

[22] Filed: Feb. 26, 1990

[51] Int. Cl.$^5$ ............................................... A61B 5/03
[52] U.S. Cl. ................................. 128/748; 128/667; 128/673; 128/675; 73/708; 250/214 C; 250/231.19; 250/238
[58] Field of Search ............... 128/667, 675, 634, 673, 128/748; 73/4 R, 705, 708; 250/227.28, 231.19, 352, 214 C, 238

[56] References Cited

U.S. PATENT DOCUMENTS

| | | | |
|---|---|---|---|
| 3,215,135 | 11/1965 | Franke | 128/675 |
| 4,487,206 | 12/1984 | Aagard | 128/675 |
| 4,678,904 | 7/1987 | Saaski et al. | 250/227 |
| 4,711,246 | 12/1987 | Alderson . | |
| 4,787,396 | 11/1988 | Pidorenko | 128/667 |
| 4,817,022 | 3/1989 | Jornod et al. | 73/4 R |
| 4,883,062 | 11/1989 | Nicholson | 128/667 |
| 4,897,542 | 1/1990 | Dakin et al. | 250/231.19 |
| 4,924,870 | 5/1990 | Wlodarczyk et al. . | |
| 4,933,545 | 6/1990 | Saaski et al. | 73/705 |

Primary Examiner—David M. Shay
Attorney, Agent, or Firm—Stetina and Brunda

[57] ABSTRACT

A catheter assembly for measuring a fluid pressure in a body cavity includes an optical converter responsive to an electrical power source for energizing a light-emitting diode which has drift characteristics which vary in response to temperature. An optical sensor is adapted to receive the light from the light-emitting diode and to provide a measurement signal indicative of the fluid pressure in the cavity. This measurement signal has undesirable characteristics related to the thermal drift characteristics of the diode. A detection circuit detects the measurement signal and provides an output signal indicative of fluid pressure in the cavity. A special filter is included in this detection circuit which has optical characteristics that substantially offset the undesirable characteristics of the measurement signal, so that the output signal is substantially independent of the temperature of the diode. A power conversion circuit enables the assembly to be energized by an excitation voltage which is provided in several different forms by various monitors.

21 Claims, 7 Drawing Sheets

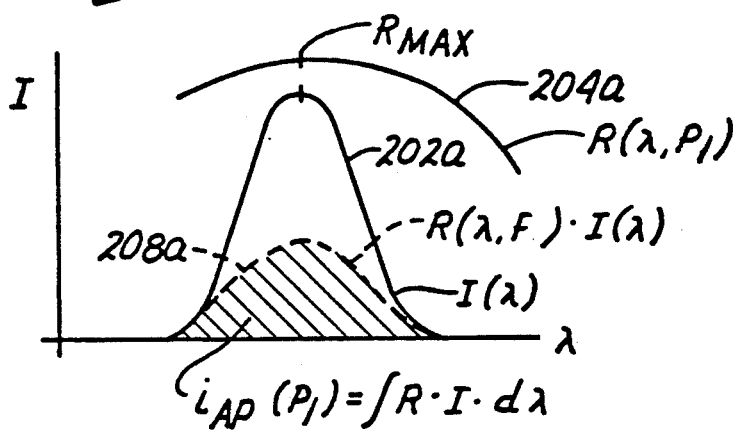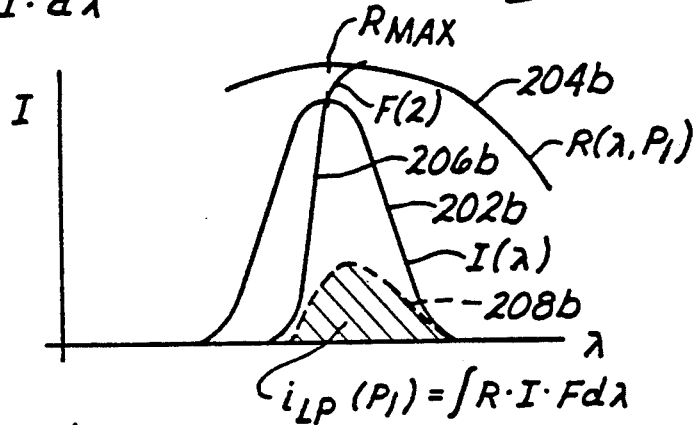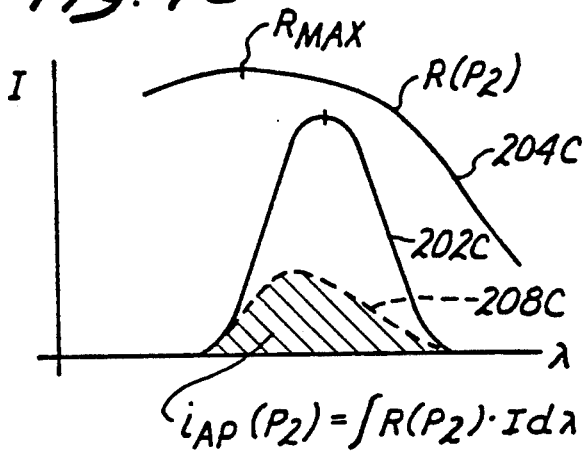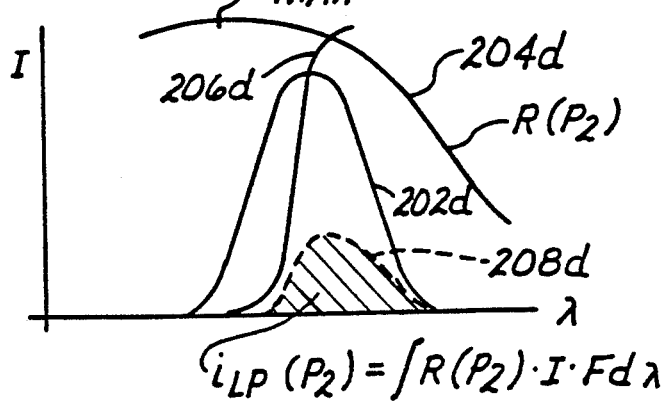

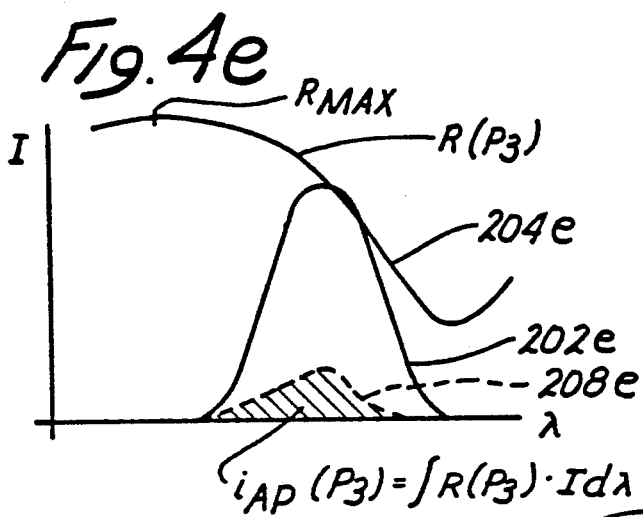
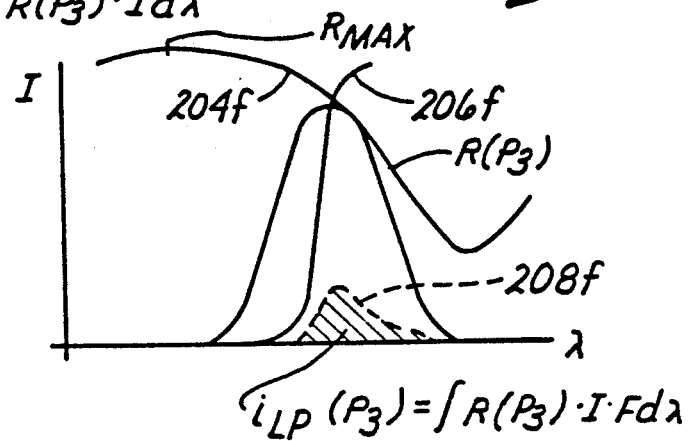
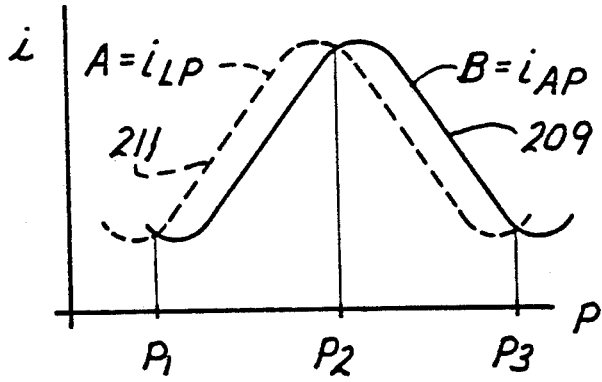
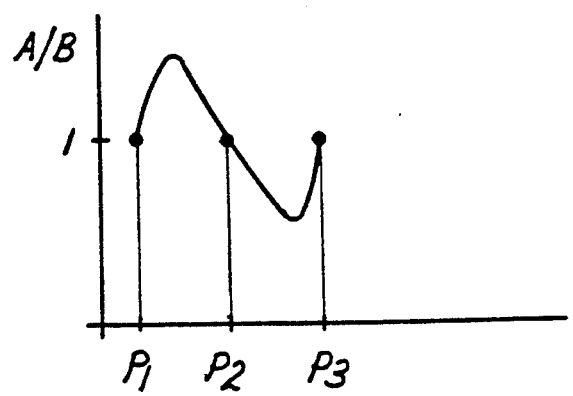

OUTPUT CIRCUIT
-120-

INTRACRANIAL PRESSURE MONITORING SYSTEM

BACKGROUND OF THE INVENTION

1. Field of the Invention

This invention relates generally to a catheter assembly for measuring fluid pressures in body cavities and more specifically to a fiber optic catheter assembly adapted for use with a variety of monitors.

2. Description of the Prior Art

Systems for measuring fluid pressure in body cavities have typically included liquid filled catheters which have communicated a fluid pressure inside the body to a pressure sensor outside the body. The accuracy of this system has suffered due to variations in hydrostatic pressure and other inconsistencies associated with the fluid column.

The sensors used with these systems have typically consisted of a pressure responsive diaphragm in fluid communication, via the fluid-filled catheter, with the body cavity. Pressure induced deflections of these diaphragms are mechanically coupled to piezo-resistive strain gauges which alter their resistance in accordance with well known principals. These strain gauges are usually configured in a Wheatstone bridge arrangement. The amount of induced strain, hence applied pressure, is determined by applying an excitation voltage to the bridge and then monitoring the bridge output voltage.

Typically the sensors are provided in a device separate from the monitor or display instrument, and are connected to the monitor via an electrical cable and a connector which may be disconnected for service, patient transfer, or disposal in the case of single patient use. Patient monitors on the other hand are often permanently installed within the operating room or intensive care unit of a hospital. These monitors often include inputs for other devices such as electrocardiogram leads.

With these systems of the past, a standard has been adopted wherein the patient monitor supplies an excitation voltage to the sensor, and the sensor provides an output voltage to the monitor. In accordance with the principles under which Wheatstone bridge sensors operate, the output voltage is proportional to the excitation voltage and also proportional to the applied voltage. Over time a proportionality constant has been standardized so that five microvolts of signal per volt of excitation is equivalent to one millimeter of mercury applied pressure. Using this standard, any sensor could be readily adapted for use with any patient monitor which also adhered to this standard.

The proportionality standard enabled users to realize a significant advantage in using these systems . . . many different types of sensors and patient monitors from various manufacturers could be readily interchanged. As a consequence, systems based on this standard, have achieved almost universal acceptance despite the difficulties associated with pressure measurements through a fluid filled catheter.

The adoption of this proportionality standard admits the possibility that the excitation voltage can be of almost any magnitude and may even be time varying. Furthermore, since the technology dictates the use of piezo-resistors having a certain minimum resistance, these sensors generally consume very little power. As a result, the monitors have been freed to supply excitation power having varying voltage levels and formats, both time-varying (sinusoidal and pulsed) and time independent (DC). This enabled excitation voltages to be supplied and configured in accordance with the requirements and desires of the individual monitor manufacturers.

The Wheatstone bridge circuits also have very low power requirements. As a result, the excitation power supplies of the monitors have been designed to provide only limited amounts of power.

Recently, applicant has disclosed an optical sensor and assembly that may be placed directly within the body cavity to be monitored. This eliminates many of the deficiencies associated with using external sensors. It is now desirable to adapt this optical catheter assembly so that it too can function with substantially all of the patient monitors presently available.

SUMMARY OF THE INVENTION

In accordance with the present invention, an optical catheter assembly is adapted for use with any monitor providing a source of excitation voltage, whether that voltage is in the form of alternating current, direct current, or pulsed current. The catheter assembly is also configured to receive these various forms of excitation voltage at substantially any of the amplitudes afforded by the various monitors presently available. In addition, this assembly is adapted to provide an output signal which is formatted substantially the same as that provided by the Wheatstone bridge strain gauges of the past.

Since the excitation power characteristics of some of the monitors are extremely low, the various circuits associated with the catheter assembly are adapted for low power consumption.

In one aspect of the invention, a catheter assembly is adapted for the measurement of fluid pressure within a body cavity of a patient. A monitor is located in proximity to the patient and provides randomly a source of excitation voltage which comprises components of at least one of a DC signal, an AC signal, or a pulsed signal. Power conversion means responsive to the random excitation voltage of the monitor provides a regulated supply of DC power which is processed for introduction to a catheter. Pressure sensor means disposed at the distal end of the catheter provides a measurement signal with characteristics indicative of the pressure in the body cavity. Ultimately display means including the monitor, detects the measurement signal from the catheter and displays on the monitor the fluid pressure in the cavity.

In another aspect of the invention, a catheter assembly includes an electrical power source and an optical converter responsive to that source for providing an optical signal. A light emitting diode included in the optical converter has thermal drift characteristics which vary in response to temperature. An optical sensor provides a measurement signal indicative of the fluid pressure which has undesirable characteristics related to the thermal drift of the diode. A detector detects the measurement signal to provide an output indicative of the fluid pressure in the cavity. A filter included in the detector has optical characteristics which substantially offset the undesirable characteristics of the measurement signal. This provides an output which is substantially independent of the temperature of the diode.

In still a further aspect of the present invention, a catheter assembly is provided with a catheter adapted for disposition in a body cavity. An optical pressure sensor is disposed at the end of the catheter and provides an optical measurement signal indicative of the fluid pressure. A detector responsive to the optical measurement signal provides an electrical signal indicative of that fluid pressure. Undesirable components of the optical measurement signal vary with temperature of the sensor but means are provided in the detector for compensating for these undesirable components.

These and other features and advantages of the present invention will be more apparent to those skilled in the art with a review of preferred embodiments discussed with reference to the following drawings.

DESCRIPTION OF THE DRAWINGS

FIGS. 4a–4n comprise a matrix of optical spectrum graphs illustrating changes in an output signal associated with an embodiment of the present invention, with variations of pressure and temperature; and FIG. 4a is a plot of the all-pass spectra at a constant temperature and a pressure P1;

FIG. 4b is a plot of the long-pass spectra at a constant temperature and a pressure P1;

FIG. 4c is a plot of the all-pass spectra at a constant temperature and a pressure P2;

FIG. 4d is a plot of the long-pass spectra at a constant temperature and a pressure P2;

FIG. 4e is a plot of the all-pass spectra at a constant temperature and a pressure P3;

FIG. 4f is a plot of the long-pass spectra at a constant temperature and a pressure P3;

FIG. 4g is a plot of the signal A and the signal B with varying pressures;

FIG. 4i is a plot of the quotient A/B with varying pressures;

FIG. 4n is a plot of the long-pass spectra at a constant pressure and a temperature T2 which affects both the LED and a filter associated with the present invention;

DESCRIPTION OF PREFERRED EMBODIMENTS

Figure 1:
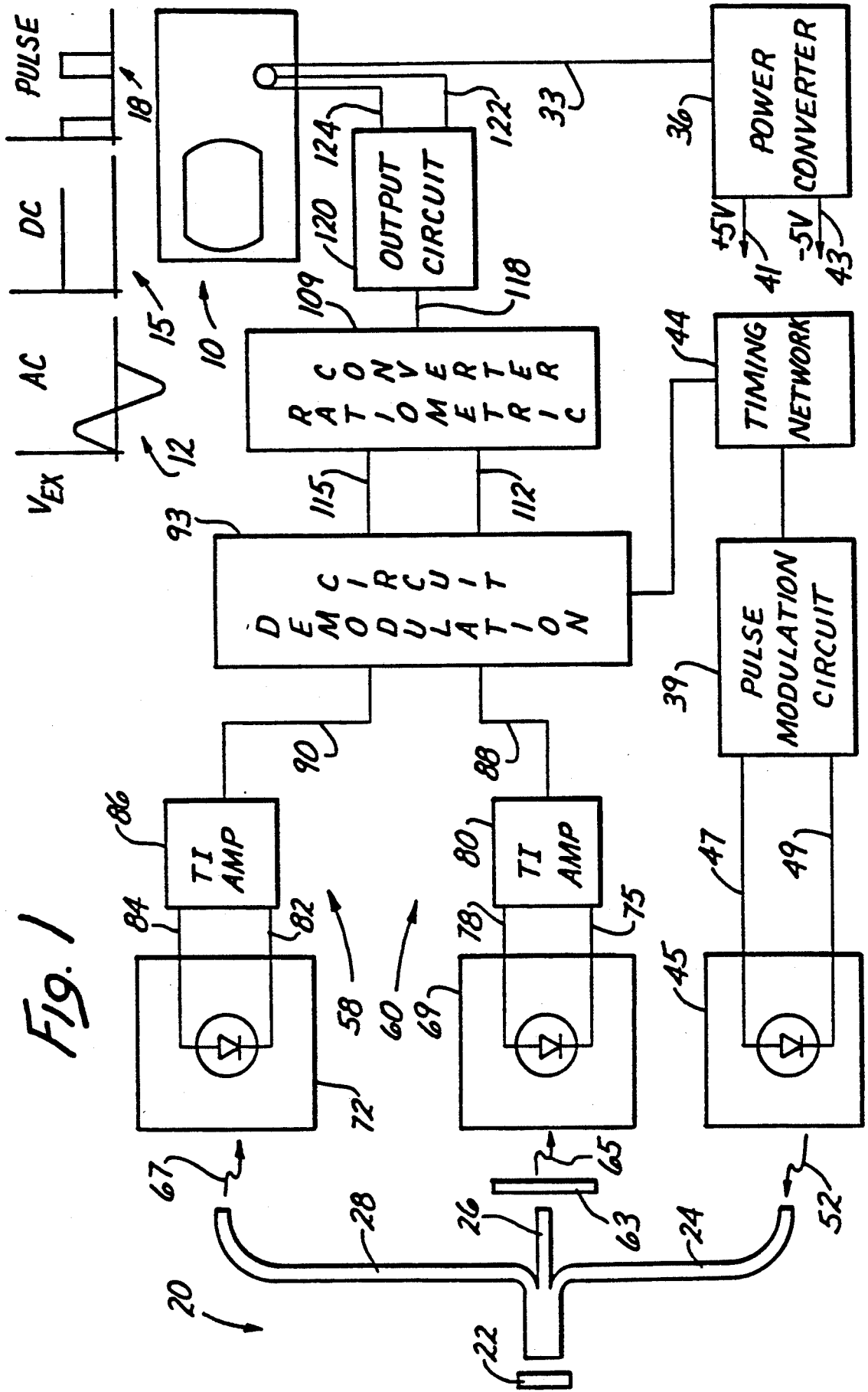
FIG. 1 is a schematic illustrating in block diagram form one embodiment of the catheter assembly associated with the present invention.

A monitor is illustrated in FIG. 1 and designated generally by the reference numeral 10. This monitor is typical of many such devices which are designed to operate with catheters (not shown) which sense pressure in body cavities using a Wheatstone bridge strain gauge. With the advent of optical pressures sensors and fiber optic technology, it is now possible to produce optical pressure catheters which operate upon the principles of optical spectral modulation. One such device which incorporates a Fabry-Perot interferometer in a reflective sensor is disclosed by applicant in his copending application Ser. No. 419,938, filed on Oct. 11, 1989 and entitled INTEGRAL INTRACRANIAL PRESSURE MONITOR AND DRAINAGE CATHETER ASSEMBLY. All aspects of the disclosure in that application are incorporated herein by reference. These optical pressure catheters and sensors provide a much higher degree of accuracy than the strain gauge sensors of the prior art.

In spite of this need to change to improved sensor and catheter technology, the industry has made a significant investment in the monitors of the past so that it is highly desirable to adapt the new catheter technology for use with the previous monitors, such as the monitor 10.

As many as 180 different types of monitors are presently in use, each providing an excitation voltage to its associated catheter, and each adapted to receive from the catheter output signals formatted in accordance with an industry standard. This standard basically requires that the signal input to the monitor be proportional to the excitation voltage with each five microvolts per volt of excitation representing a pressure equal to one millimeter of mercury. This standard can be better understood with reference to Table I which provides other examples of excitation voltage, input signal and resulting pressure.

TABLE I

| $V_{ex}$ | Signal | | Pressure |
|---|---|---|---|
| 5 VDC | 25 μV | = | 1 mmHg |
| 5 VDC | 50 μV | = | 2 mmHg |
| 10 VDC | 50 μV | = | 1 mmHg |
| 5V$_{rms}$@5kHz | 50 μV$_{rms}$ | = | 2 mmHg (in phase with excitation) |

This industry standard of 5 microvolts/$V_{ex}$/mmHg, has provided a design specification for most of the monitors presently in use. In order for any catheter to cooperate with such a monitor it must provide a signal in accordance with this standard in order for the monitor to display the proper pressure readings.

Although the monitors, such as the monitor 10, are adapted to receive a similar input signal, they vary greatly in their provision of an excitation voltage. Many of the monitors, such as those manufactured by Hewlett-Packard, provide an excitation voltage in the form of AC signal such as that illustrated at 12 in FIG. 1. This AC signal 12 may have a voltage of 3.7 V$_{rms}$ at 2.4 kHz, for example. Other monitors, such as those manufactured by Siemans, provide an excitation voltage in the form of a DC format signal as shown by the reference numeral 15. This signal 15 may have a voltage of 2.5 volts DC. In comparison, the monitors manufactured by Tektronix provide an excitation voltage in a pulse format (illustrated at reference numeral 18), where each of the pulses has an amplitude of 7 volts and a duration of 20 milliseconds. A catheter and sensor configured to receive their only power from these random monitors, such as the monitor 10 must be adapted to receive that power in any one or a combination of these formats represented by the AC signal 12, the DC signal 15 and- /or the pulse signal 18. Furthermore, the signal returned to the monitor must be proportional to the instantaneous value of the excitation voltage.

The catheter of the present invention is shown generally at 20 in FIG. 1. At the distal end of the catheter 20, an optical pressure sensor 22 is provided which receives an input optical signal along a fiber optic conductor 24 and provides a return optical signal representative of pressure along fiber optic conductors 26 and 28. In a particular embodiment, the fiber optic conductors 24, 26 and 28 may be a single conductor as illustrated in FIG. 1. An electronic circuit disposed between the catheter 20 and the monitor 10 is adapted to generate an optical signal from the excitation voltage of the monitor 10 and to detect the return optical signal from the catheter 20 in a format which is compatible with the monitor 10. In this manner, the fiber optic pressure catheter 20 can be connected solely to the monitor 10 without any extraneous electrical power requirement or signal input. In the illustrated embodiment the catheter 20 and associated electronics are connected directly to the monitor 10, for example at a connector 30, to receive the excitation voltage from the monitor 10 and to supply the output pressure signal to the monitor 10.

The excitation voltage is received along a conductor 33 and introduced to a power converter 36 as discussed in greater detail with reference to FIG. 2. This power converter 36 is adapted to receive the excitation voltage in any of the formats shown at 12, 15, 18, or a combination thereof, to provide a supply of power at plus 5 volts DC and at minus 5 volts DC. These voltages, which are provided regardless of the format or the magnitude of the excitation voltage, are made available throughout the system on conductors 41 and 43 to power the electronic circuits discussed below.

Another circuit which serves the entire monitoring system is a timing network 44 which provides a timing signal that coordinates the electronic circuits throughout the system. In a preferred embodiment, the network 39 provides clock pulses at a frequency of 500 KHz.

One such circuit is a pulse modulation circuit 39 which supplies power to the catheter 20 and associated electronics in a pulse format. Such a format provides power only for the duration of each pulse, and therefore significantly reduces the power requirements of the system. This is particularly desirable in view of the very limited power being supplied by the typical monitor 10 in its excitation voltage. In a preferred embodiment the pulse modulation circuit 39 provides power in a pulse format with the pulse having an amplitude of 40 mA and a duty cycle of 1.6%. This power is introduced to an output LED 45 across conductors 47 and 49.

The LED 45 responds to the pulsed power from the circuit 39 by producing a pulsed optical signal illustrated by an arrow 52. This signal 52 is introduced into the fiber optic conductor 24 of the catheter 20. In the conductor 24 the optical signal 52 interrogates the sensor 22 which provides a return optical signal on the fiber optic conductors 26 and 28. This operation of the catheter and the sensor 22 is discussed in greater detail in applicant's copending application U.S. Ser. No. 419,938.

A detection circuit, shown generally at 55, receives this optical signal, detects it for the pressure information, and places it in a format suitable for introduction to the monitor 10. The detection circuit 55 of this embodiment includes two legs 58 and 60 which are configured to receive, detect and integrate over time, the pulsed optical signal. In the case of leg 58, the optical signal is received directly from the sensor 22 along the fiber optic conductor 28. In the case of the leg 60, the optical signal is received from the sensor 22 along the fiber optic conductor 26 but is directed through an optical filter 63 before introduction to the detection circuit 55. As discussed in greater detail with reference to FIG. 4, the filter 63 is chosen with properties which are keyed to those of the LED 45 i n order to compensate for undesirable temperature characteristics in the return signal. This return signal, corrected by the filter 63, is referred to as the long-pass signal and is illustrated by an arrow 65. The unfiltered signal from the conductor 28 is referred to as the all-pass signal and is illustrated by an arrow 67. These optical signals 65 and 67 are directed onto respective photo diodes 69 and 72 in the detection circuit 55.

The electrical signal from the photo diode 69 is introduced across conductors 75 and 78 to a transimpedance amplifier 80. Similarly, the signal from the photo diode 72 is introduced across conductors 82 and 84 to a transimpedance amplifier 86. These amplifiers 80 and 86 transform the current received across their respective conductor pairs 75, 78 and 82, 84 into voltages which are output onto respective conductors 88 and 90. The voltages on these conductors 88 and 90 are received by a demodulation circuit 93 to a ratiometric converter 109 along respective conductors 112 and 115. As discussed in greater detail with reference to FIG. 3, the ratiometric converter 109 ratios the respective signals on conductor 112 and 115 to automatically compensate for the undesirable temperature characteristics in the return signal. The resulting signal is appropriately scaled so that zero pressure on the sensor 22 results in a signal which is displayed as zero pressure on the monitor 10.

This signal is introduced on a conductor 118 to an output circuit 120 which provides for further modification to the zero adjustment. This insures that the final output signal on a pair of conductors 122 and 124 signifies zero voltage at zero pressure. This output signal is introduced through the connector 30 to the monitor 10 for appropriate display.

Figure 2:
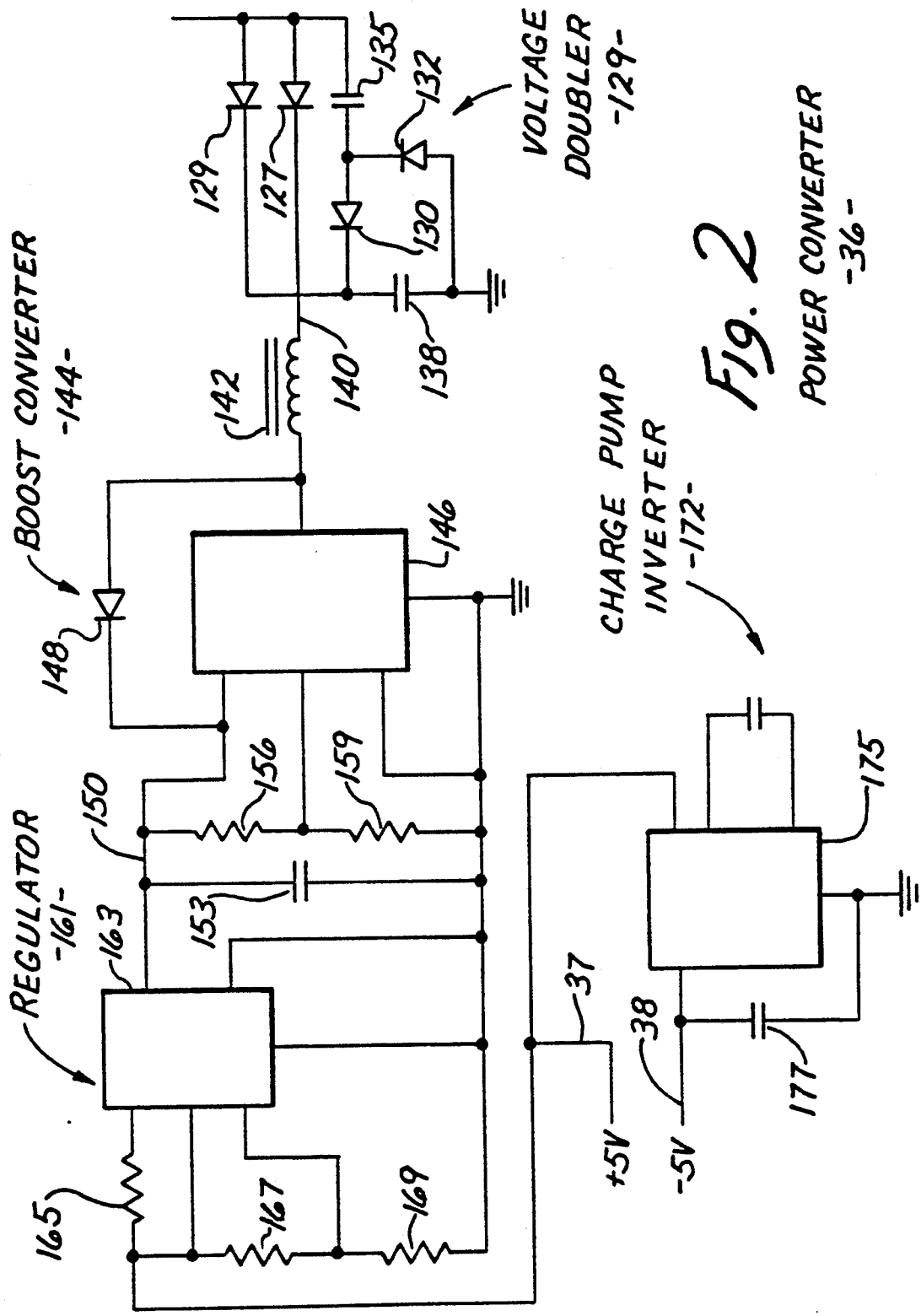
FIG. 2 is a schematic partially in block diagram form of a power conversion circuit associated with an embodiment of the present invention.

The importance and function of the power converter 36 can be more easily understood with reference to FIG. 2. The converter 36 receives the excitation voltage from the monitor 10 on conductor 33 previously discussed. This voltage is input into a pair of diodes 125, 127, and also to a voltage doubler circuit shown generally at 129. The doubler 129 also includes a pair of diodes 130, 132 and a pair of capacitors 135 and 138 connected in the traditional manner as illustrated in FIG. 2. If the excitation voltage is in a DC or pulse format as illustrated at 15 and 18 respectively in FIG. 1, that voltage will pass through the diodes 125 and 127 onto a conductor 140. In a preferred embodiment, the diodes 125, 127, 132 and 135 are of the Schottky type chosen to minimize voltage drop and power loss.

If the excitation voltage is provided in a AC format as illustrated at 12 in FIG. 1, the voltage doubler 129 rectifies and filters that voltage to a DC format, and the resulting signal is introduced onto the conductor 140.

An inductor 142 receives the power supply on conductor 140 which functions to boost the voltage from the introductory circuit. As current through the inductor 142 is reduced, for example at the trailing edge of a pulse, this inductor 142 tends to maintain that current by increasing the voltage. The resultant signal is introduced into a boost converter 144 to further enhance the magnitude of the power supply. In a preferred embodiment, the boost converter 144 comprises a chip 146, such as Maxim model no. MAX631ACPA, which contains an internal bypass diode (not shown). In a preferred embodiment, an additional diode 148 is paralleled to reduce power loss.

It is desirable that the converter 144 receive an input voltage of at least 2 volts DC in order for it to function properly. Acknowledging appropriate resistance drops for the diodes 125, 127, 130 and 132, it is desirable that the input excitation voltage $V_{ex}$ from the monitor 10 be at least 2.3 volts.

It is the function of the boost converter 144 to raise the input voltage, such as 2 volts DC, to an amplitude of about 6 volts DC. If the voltage input to the converter 144 is greater than 6 volts DC, it will bypass the amplification provided by the chip 146 and pass directly through the internal diode (not shown) and the diode 148. The resultant signal of at least 6 volts DC is output on a conductor 150 which is appropriately filtered by an output capacitor 153. A pair of resistors 156 and 159 provide a feedback control circuit for setting the output of chip 146.

The signal on conductor 150 is introduced to a regulator shown generally at 161. It is the function of regulator 161 to receive the voltage from converter 144, which has a magnitude of at least 6 volts DC, and to regulate that voltage to a positive 5 volts DC. The regulator 161 includes a chip 163 which in a preferred embodiment is a Maxim model no. of ICL7663CPA. The output chip 163 is directed through a current limiting resistor 165. Resistors 167 and 169 form part of a feedback control circuit for chip 163 which provides its output on conductor 41, previously discussed with reference to FIG. 1.

In order to produce the minus 5 volt DC signal on the conductor 43, the plus 5 volt DC signal on conductor 41 is introduced to a charge pump inverter shown generally at 172. This inverter 172 may include a chip 175 such as Maxim ICL7660CPA. A charge capacitor 177 associated with the inverter 172 flips the input positive voltage so that a voltage with a same magnitude but a reverse polarity is introduced on the conductor 43. In this manner, the charge pump inverter 172 provides the minus 5 volt DC signal which is available throughout the monitoring system.

In response to these supply voltages on the conductors 41 and 43, the pulse modulation circuit 39 produces a series of pulses which are output on conductor 47 to pulse LED 45. The optical signal represented by arrow 52 is then introduced to catheter 20 as a pulsating light signal. In a preferred embodiment, the electrical signal on conductor 47 has an amplitude of 40 mA and a pulse duty cycle of 1.5%.

Figure 3:
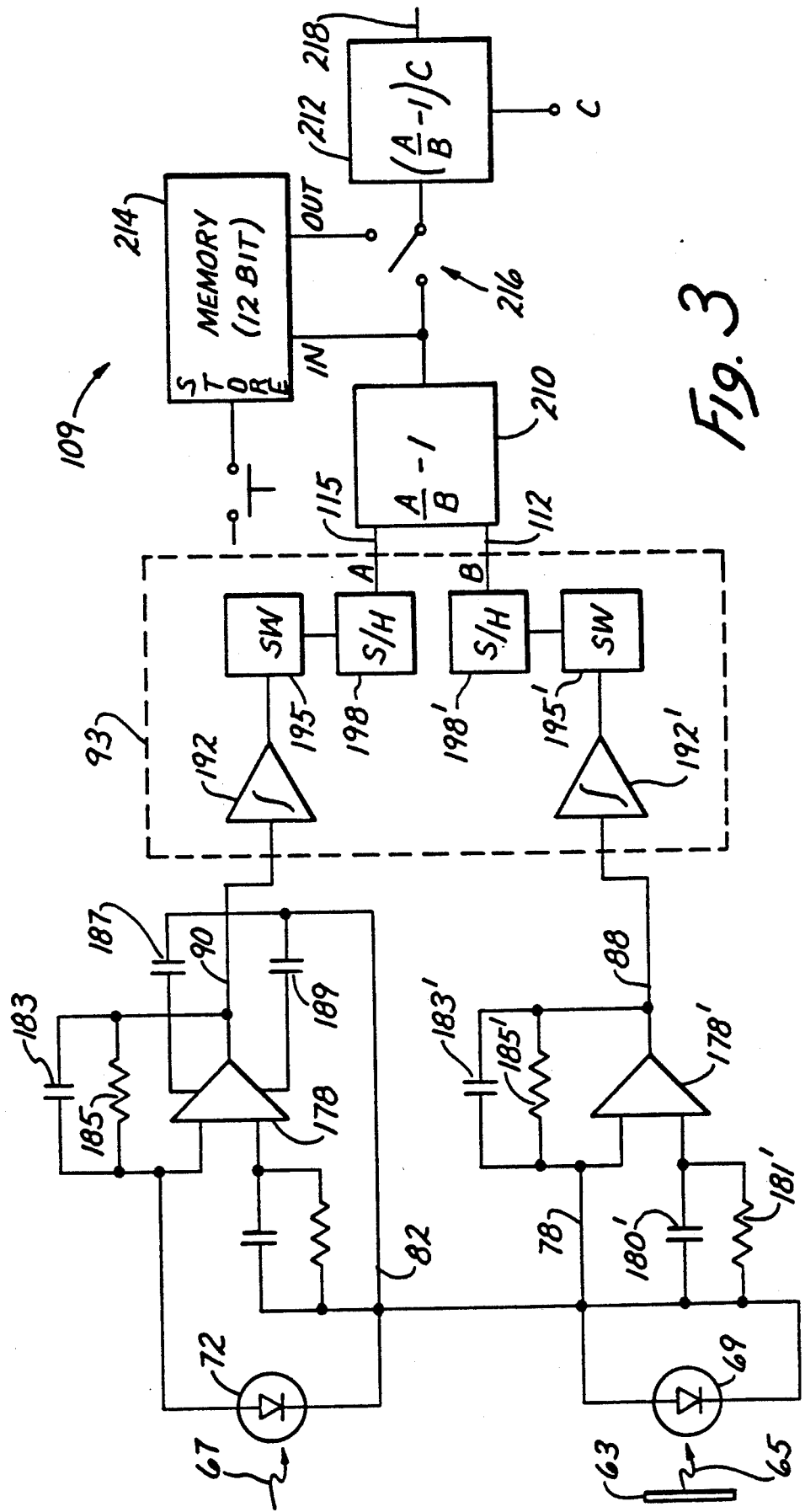
FIG. 3 is a schematic partially in block diagram form illustrating the detection, demodulation and ratiometric circuits associated with a preferred form of the present invention.

With the exception of the output circuit 120, the electronics associated with the return signal are illustrated in greater detail in FIG. 3. Thus, the all-pass photo signal 67 is directed onto the photo diode 72 and the long-pass signal 65 is directed onto the photo diode 69. Referring only to the leg 58, the electrical signal from the diode 72, which is presented across conductors 82 and 84 is introduced to a preamp 178. A conductor 82 is biased through a resistor 181 in order to minimize preamp offsets. The output of preamp 78 is directed onto conductor 90, but a feedback circuit including the parallel combination of a capacitor 183 and a resistor 185 carries the output signal back to the conductor 84. It is the resistor 185 which provides the primary characteristics associated with transimpedance amplifier 86. More specifically, the output on conductor 90 is a negative voltage equal to the value of the input current multiplied by the impedance of resistor 185. The preamp 178 in a preferred embodiment is a model LT1078ACN8 with supply voltages appropriately filtered by a pair of decoupling capacitors 187 and 189.

Components performing similar functions to those in the leg 58 are designated by the same reference numeral primed in leg 60. Thus, the output on conductor 88 is a negative voltage equal to the magnitude of the input current on conductor 78 multiplied by the impedance of resistor 185'.

In the demodulation circuit 93, an integrator 192 provides an output proportional to the voltage on conductor 90 multiplied by the LED pulse time. This output of the integrator 192 is introduced to a switch circuit 195 which is synchronized to the timer in pulse modulation circuit 39. The resulting signal is processed in a sample and hold circuit 198 and introduced onto conductor 115. In the following discussion this signal is referred to as the all-pass signal A.

In the leg 60, these circuits 192, 195 & 198 are duplicated and designated with the same reference numerals primed, 192', 195' & 198 '. Thus, the signal from the sample-and-hold circuit 198' in the leg 60' is introduced onto conductor 112. In the following discussion, this signal is referred to as the long-pass signal B.

Figure 4H:
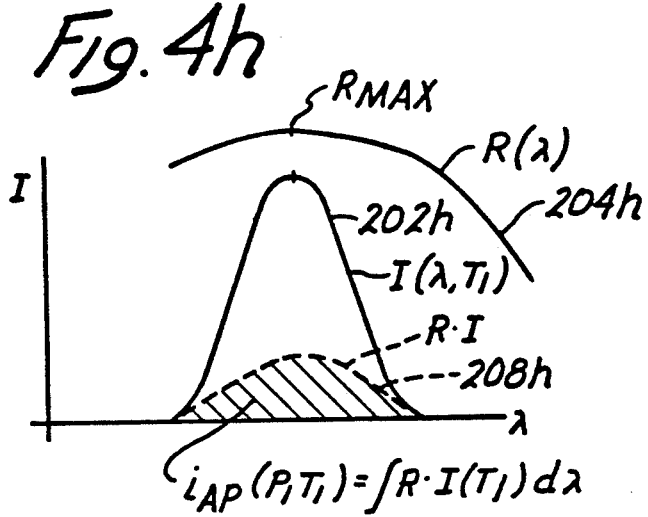
FIG. 4h is a plot of the all-pass spectra at a constant pressure and a temperature T1.
Figure 4J:
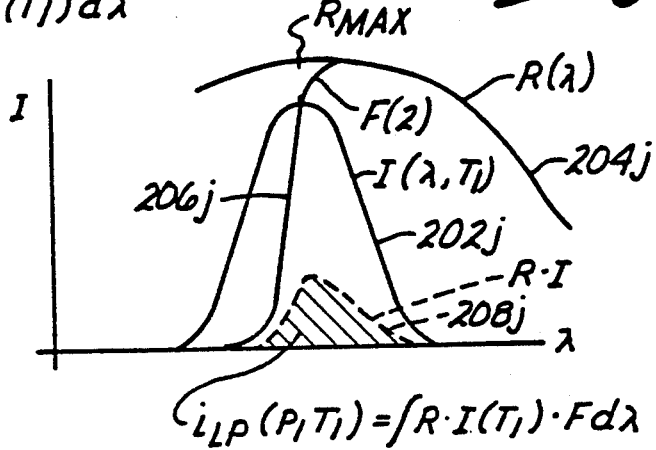
FIG. 4j is a plot of the long-pass spectra at a constant pressure and a temperature T1.
Figure 4K:
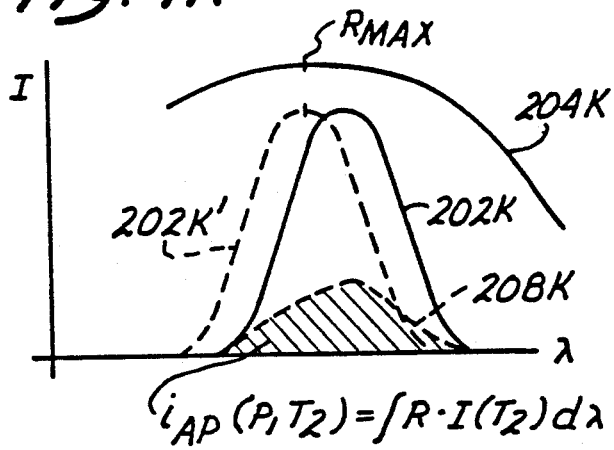
FIG. 4k is a plot of the all-pass spectra at a constant pressure and a temperature T2.
Figure 4M:
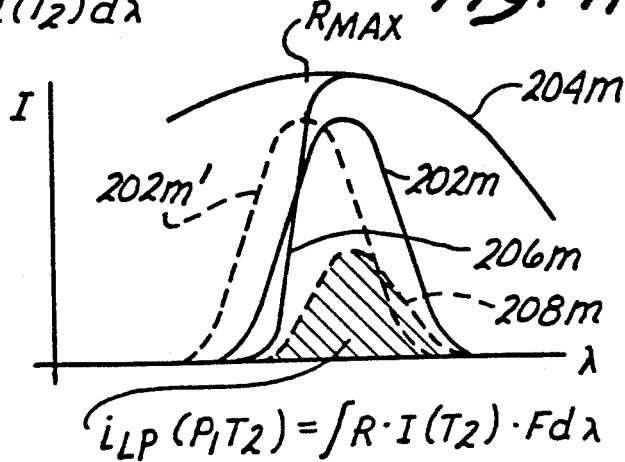
FIG. 4m is a plot of the long-pass spectra at a constant pressure and a temperature T2 which affects only an LED associated with the present invention.
Figure 4N:
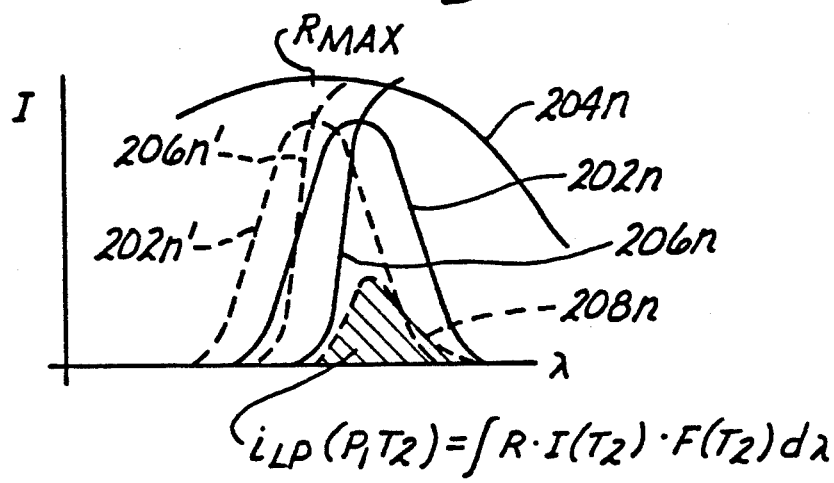

The processing of signals through the transimpedence amplifiers 80, 86, the demodulation circuit 93 and the ratiometric converter 109 can be best understood with reference to FIG. 4, which is subdivided into FIGS. 4a–4n. Each of these FIGS. 4a–4n illustrates various spectral frequencies with variations in temperature and pressure.

In FIG. 4, three spectra are of particular interest:
1) The spectrum associated with the light emitting diode 45, designated by the reference numeral 202;
2) The spectrum associated with the reflectance of the sensor 22, designated by the reference numeral 204; and
3) the spectrum associated with the filter 63, designated by the reference numeral 206.

These spectrum, which may differ in the various figures, will be designated by the foregoing sequence numerals 202, 204 & 206 and also by the letter of their respective figures. Thus, the spectrum associated with the LED 45, will be designated by the reference numeral 202a in FIG. 4a and by the reference numeral 202b in FIG. 4b.

The graphs of FIGS. 4a–4g illustrate spectral shifts under conditions of constant temperature and varying pressure. Thus, the LED spectrum 202a is illustrated to have its peak generally centered on the peak or maximum value $R_{max}$ of the sensor spectrum 204a. In the all-pass leg 58 of the circuit, the signal which actually occurs on the conductor 84 is the wavelength integral of the product of these two spectra 202a and 204a. The combination spectrum is designated 208a in FIG. 4a and is derived by multiplying the instantaneous values of the spectra 202b and 204b at each of the wavelengths in the spectrum.

During the LED pulse on time, the photo detector 72 outputs a current which is proportional to the area under the combination spectrum 208a. As a result of the operation of demodulator 93, a signal is present on conductor 115 which is representative of the value of the area under the combination spectrum 208a averaged over the LED pulse on time interval. This signal is updated during each LED pulse. At pressure P1 this area is given by the formula illustrated in FIG. 4a.

In FIG. 4b these same spectra 202b and 204b represent the signals in the long-pass leg 60 and also appear with their peaks generally aligned for the pressure P1. The long-pass leg 60 differs from the all-pass leg 58 solely by the provision of the filter 63 which is disposed between the sensor 22 and the LED 69. This filter 63 adds to the analysis its spectrum which is designated by the reference 206b in FIG. 4b. As in the leg 58, these spectra 202b, 204b and 206b multiply to provide the combination spectrum 208b on conductor 78. As in the previous case, the combination spectrum 208b is derived by multiplying the instantaneous values of the spectra 202b, 204b as well as the spectrum 206b at each of the wavelengths in the spectrum. As a result of the integration accomplished in the demodulation circuit 93, the signal on conductor 112 represents the area beneath the combination spectrum 208b averaged over the LED pulse on-time interval, and is characterized by the formula illustrated in FIG. 4b.

Since the whole purpose of the system is to monitor pressure change, it is not surprising that a change in pressure dramatically changes the relationship of these spectra. A change from pressure P1 to a greater pressure P2 is illustrated in FIGS. 4c and 4d for the respective all-pass and long-pass legs 58 and 60. Since a change in pressure does not affect the intensity of the LED 45, the LED spectrum 202c remains the same. It is the sensor 22 which experiences the pressure change and responds with a dramatic shift to the left of the sensor spectrum 204c. Of course the product of these two signals must also change, so the combination spectrum 208c now appears less symmetrical than the spectrum 208a with its peak also shifting to the left. More importantly, the area beneath this combination spectrum 208c is significantly reduced. At the pressure P2 this area for the all-pass leg 58 is represented by the formula illustrated in FIG. 4c.

FIG. 4d illustrates the same shift of the LED spectrum 204d, but the filter spectrum 206d does not shift with the change to pressure P2. A product of the three spectrum 202d, 204d and 206d results in the combination spectrum 208d which is shifted slightly to the left from its position in FIG. 4b. At the pressure P2, the signal on conductor 112 varies with the area beneath this combination spectrum 208d and is represented by the formula illustrated in FIG. 4d.

If the pressure increases even further, for example to a pressure P3, the sensor spectrum 204 will shift even further to the left as illustrated at 204e in FIG. 4e. Since this spectrum 204e has a dramatic change in shape along its right side, its instantaneous wavelength values dramatically affect the shape of the product or combination spectrum 208e. Of course, the area beneath the combination spectrum 208e also changes dramatically and is as represented by the formula illustrated in FIG. 4e.

Referring to FIG. 4f, a further shift of the sensor spectrum 204f with an increase to pressure P3, also dramatically affects the area beneath the combination spectrum 208f which is represented by the formula illustrated in FIG. 4f.

An overview of FIGS. 4a, 4c and 4e illustrates that a change in pressure from P1 to P3 results in a slight change in the area beneath the combination spectrum 208 in the all-pass leg 58. This change can be plotted against pressure to illustrate that the change is generally sinusoidal as shown by a signal 209 in FIG. 4g. This is actually the all-pass signal B which occurs on conductor 115.

FIGS. 4b, 4d and 4f which relate to the long-pass leg 60, show a similar change in the area beneath the curve 208 even when the filter spectrum 206 is added to the leg. Once again, the changes in the area beneath the combination spectrum 208 can be plotted against pressure to show a generally sinusoidal curve designated by the reference numeral 211 in FIG. 4g. This is actually the long-pass signal A which occurs on conductor 112.

A comparison of the A signal and B signal indicates that they are generally similar in shape but tend to be slightly out of phase. This results from the presence of the filter 63 in the long-pass leg 60 which adds the spectrum 206 to the analysis. Since the filter spectrum 206 occurs slightly to the right of the maximum value for the LED spectrum 202, the maximum area for the combination spectrum 208 tends to occur at a slightly lower pressure than it does in the all-pass leg 58. Although these changes in magnitude and phase differ only slightly with pressure, a dramatic difference occurs when the signal A is divided by the signal B.

This twin spectral band ratiometric technique has a number of significant advantages which are shown in a plot of the quotient A/B with varying pressures. This plot is illustrated in FIG. 4g'. It will be first noted that, the A/B ratio signal is significantly more linear in a portion of its range than either the A or B signals. This allows the system to use the A/B ratio signal directly without any additional linearization, provided the applied pressures are restricted to this range. Second, since variations in LED intensity—which may be due to aging, input power variations, or optical coupling efficiency—generally affect all wavelengths, equally, it follows that both the A and B signals are affected equally. Thus, the ratiometric signal A/B is substantially independent of the optical power output of the LED. Third, optical power losses due to imperfections in optical connections and bending of the optical fibers, generally affect all wavelengths equally. Providing the ratiometric signal A/B tends to neutralize these variations leaving the signal generally unaffected by these optical power losses.

The foregoing reference to FIGS. 4a–4g has illustrated how a slight change in pressure at the sensor 22 can result in a significant change in the resulting quotient A/B. It will now be shown with reference to FIGS. 4h to 4n that changes in temperature can produce an undesirable effect on the monitoring signals.

FIG. 4h illustrates that at a given temperature T1 and constant pressure P1, the LED spectrum 202h and sensor spectrum 204h may be generally aligned as previously discussed with reference to FIG. 4a. Multiplying these spectra 202h and 204h in the all-pass leg 58 produces the combination spectrum 208h which has an area represented by the formula illustrated in FIG. 4h. The combination spectrum 208h is similar in size and shape to the spectrum 208a discussed with reference to FIG. 4a.

FIG. 4j illustrates that at the temperature T1 the long-pass leg 60 which includes the filter 63 will produce a combination spectrum 208j. This spectrum 208j is similar in size and shape to that illustrated in FIG. 4b at the pressure P1.

Assuming this pressure P1 is held constant, and the temperature changes from T1 to T2, it can be seen that the combination spectrum 208 will also change. This change is illustrated in FIGS. 4k and 4m for the respective all-pass leg 58 and long-pass leg 60.

In FIG. 4k, the spectrum 204k is unchanged since the output of the sensor 22 varies only with pressure. However, the spectrum 202k associated with the LED 45 which is sensitive to temperature, tends to shift to the right. The product of these two spectra 202k and 204k results in a change of shape for the combination spectrum 208k. And since the area beneath this spectrum 208k is being monitored, a change in the temperature also produces a change in the signal on conductor 115. This A signal is represented by the formula illustrated in FIG. 4k.

FIG. 4m illustrates that a change in temperature from T1 to T2 shifts the LED spectrum 202m to the right. Thus the characteristics of the LED 45 result in a change from the dotted line 202m prime to the solid line associated with the spectrum 202m. This shift is relative to both the sensor spectrum 204m and the filter spectrum 206m which do not vary with temperature. Under these circumstances, the combination spectrum 208m actually increases in size. This area is represented by the formula illustrated in FIG. 4m.

A detailed comparison of the all-pass signals A illustrated in FIGS. 4h and 4k indicates that there is relatively little change with respect to temperature. Thus, there is generally equality as shown by the following Formula I.

$$i_{AP}(P_1T_1) = i_{AP}(P_1T_2) \qquad \text{(Formula I)}$$

By comparison, the long-pass signal B changes dramatically with temperature as illustrated by the following Formula II.

$$i_{LP}(P_1T_1) << i_{LP}(P_1T_2) \qquad \text{(Formula II)}$$

It follows from Formula I and Formula II that the quotient of signal A divided by signal B also changes significantly with temperature as indicated by the following Formula III.

$$\left.\frac{A}{B}\right|_{T_1} = \left.\frac{i_{LP}}{i_{AP}}\right|_{T_i} << \left.\frac{i_{LP}}{i_{AP}}\right|_{T_2} = \left.\frac{a}{B}\right|_{T_2} \qquad \text{(Formula III)}$$

This variation in the pressure signal as a result of a change in temperature can result in undesirable signal changes as great as five percent of full scale output per degree centigrade. If full scale is equivalent to 100 millimeters of mercury, a 5 percent variation would be equivalent to 5 millimeters of mercury per degree centigrade. If one desires to maintain even one millimeter of mercury stability, which is typical, it would be necessary to control the temperature of the LED 45 to within 1/5th of a degree centigrade. The prior art has attempted to provide this control by actually placing the LED 45 in a control led temperature environment. These attempts have been generally ineffective even though they have increased significantly the cost and complexity of the system, and have required significantly more electrical power than provided by monitor 10.

With reference to FIG. 4n, it is illustrated that the filter 63 can be chosen with characteristics which also vary with temperature. In fact, the filter 63 can be chosen so that its temperature characteristics are quite similar to those associated with the LED 45. In a preferred embodiment, the filter 63 provides a shift of its spectrum 206m which varies with temperature to about the same extent as the LED spectrum 202m. In FIG. 4n these spectral shifts are illustrated with a change from the dotted line 202m' to the solid line of spectrum 202n, and from the dotted line 206m' to the solid line of spectrum 206m. Since both of the spectra 202m and 206m are shifting, the change in the area beneath the combination spectrum 208m is relatively insignificant. What change there is can be attributed almost solely to the non-linear shape of the sensor spectrum 204m. A comparison of the combination spectrum 208j in FIG. 4j and the combination spectrum 208n in FIG. 4n would indicate that there is little change in the long-pass signal B resulting from changes in temperature. This is shown by the following Formula IV.

$$i_{LP}(T_1) \approx i_{LP}(T_2) \qquad \text{(Formula IV)}$$

If the all-pass pressure signal A does not change significantly with temperature, as illustrated by Formula I, and the long-pass signal B does not change significantly with temperature, as illustrated by Formula IV, it follows that the quotient A over B will also remain generally constant with temperature as illustrated by the following Formula V.

$$\left.\frac{A}{B}\right|_{T_1} = \left.\frac{i_{AP}}{i_{LP}}\right|_{T_i} << \left.\frac{i_{AP}}{I_{LP}}\right|_{T_2} = \left.\frac{a}{B}\right|_{T_2} \qquad \text{(Formula V)}$$

In practice it has been found that the undesirable components of the pressure signal A/B which vary with temperature, can be reduced to approximately 0.5 percent of the full scale output per degree centigrade. Thus the undesirable temperature components can be reduced by a factor of ten by choosing the filter 63 with appropriate temperature characteristics. If these characteristics are chosen to coincide generally with the temperature characteristics of the LED 45, the only change in the pressure signal A/B will be due generally to the shape of the sensor spectrum 204m which is slightly curved rather than flat. Even these affects can be minimized by maintaining the spectrums of the LED 45 and filter 63 in the generally linear portions of the sensor spectrum 204.

As previously mentioned, the all-pass signal A is presented on conductor 115 and the long-pass signal B is presented on conductor 112. In this illustrated embodiment, these signals are introduced to a divider network 210 as shown in FIG. 3. In this network 210, the signal A is divided by the signal B and a constant value is subtracted from the quotient. This value is the estimate of the zero pressure ratio $A_o/B_o$, and serves to reduce the magnitude of the resultant signal to a valve that can be accommodated by the various monitors, such as the monitor 10. The value is digitized to provide a 12-bit digital signal. This digital signal is introduced to a multiplier network 212 which multiplies the quantity $[(A/B)-1]$ by a factor C which scales the signal. In a preferred embodiment this is accomplished through a series of digitally actuated resistive gates which produce the resultant signal $[(A/B)-1](C)$ in analog form.

In a preferred embodiment, the multiplicative factor C is made to be proportional to the instantaneous value of the excitation voltage supplied by the monitor 10. Thus, the resulting analog signal $[(A/B)-1](C)$ is both proportional to the excitation voltage supplied by the monitor 10 and also to the applied pressure as required by the monitor 10. Thus by suitably choosing the scaling factor, the combined signal [(A/B)−1](C) can also be scaled to the industry standard of five microvolts per volt per millimeter of mercury.

One reason for initially converting the signal to a digital format in the network 210 and then converting the signal to an analog format in the network 212 is to facilitate storage of a quantity representative of zero pressure. For this purpose, a 12-bit memory bank 214 is provided. When the pressure on the sensor 22 is Known to be zero, this memory bank 214 can be switched to store the output of the divider network 210. If it becomes desirable to disconnect the catheter 20 from a monitor 10 in one location such as the operating room, it can be reconnected to a different monitor 10 in another location, such as a critical care room. Under these circumstances, the digital signal in the memory 214 can be introduced through a switch 216 to zero the new monitor.

Figure 5:
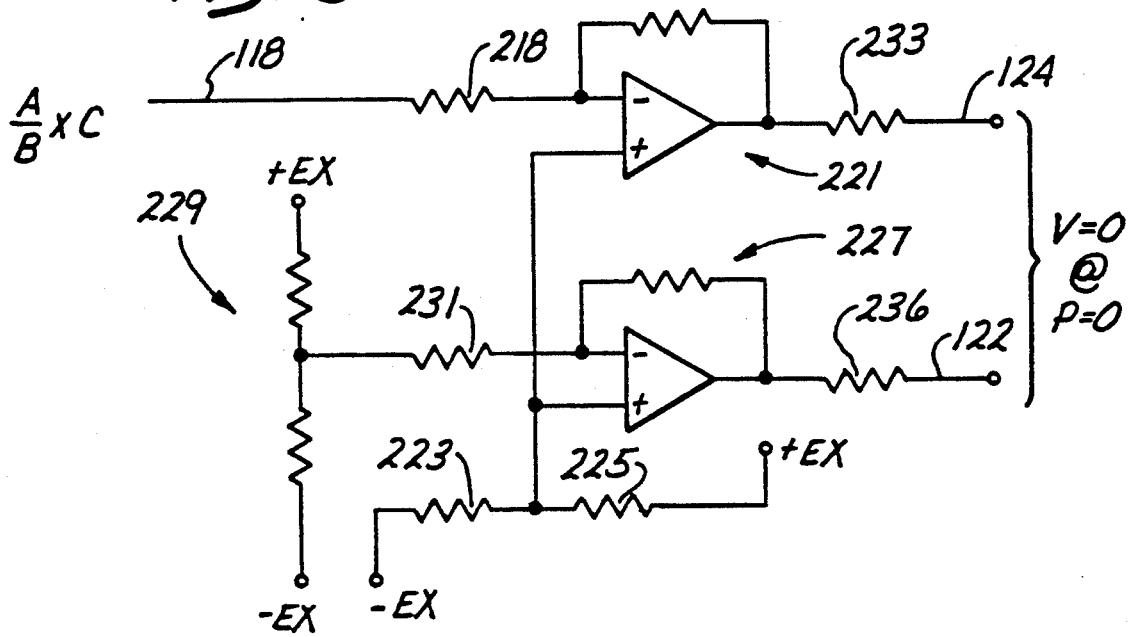
FIG. 5 is a schematic diagram of an output circuit associated with a preferred embodiment of the present invention.

The analog signal on the conductor 118 is introduced to the output circuit 120 which is illustrated in greater detail in FIG. 5. The conductor 118 is connected through a resistor 218 to an operational amplifier shown generally at 221. The positive input to this amplifier 221 is appropriately biased between the two excitation voltages by a pair of resistors 223 and 225. The same bias is applied to the positive input of a second operational amplifier 227. A potentiometer 229 placed across the two excitation voltages provides input through a resistor 231 to the negative terminal of the amplifier 227. The potentiometer 229 can be adjusted to provide a gross zero adjustment for the catheter 20. This adjustment typically would be fixed by the manufacturer so that any deviations from zero could be accomplished by adjusting the monitor 10. The output of the operational amplifiers 221 and 227 is directed through respective output resistors 233 and 236 on conductors 124 and 122. The final output signal presented across these conductors 122 and 124 is introduced through the connector 30 to the monitor 10. With suitable zero adjustments the monitor 10 will display a zero value when the sensor 22 is disposed in a zero pressure environment.

The optical catheter 20 and associated electronics is operable with many types of monitors 10 regardless of the format of the monitor's excitation power and in spite of the fact that these monitors have been designed for use with strain gauge sensors. The signals presented by the optical catheter 20 are corrected for temperature so that variations in the signal are dependent almost entirely upon variations in the pressure of the fluid surrounding the sensor 22.

Although this invention has been disclosed with reference to specific embodiments, it will be understood by those skilled in the art that the invention can be otherwise embodied so that the scope of the invention should be ascertained only with reference to the following claims.

What is claimed is:

1. An apparatus for sensing a physical parameter including:
   a sensor exhibiting a physical change in response to the physical parameter;
   a source of light disposed in a particular environment and providing an incident light signal having undesirable properties which vary in response to a change in temperature in the particular environment;
   means for directing the incident light signal onto the sensor and receiving a reflective light signal from the sensor, the reflective light signal having first characteristics dependent upon the physical change of the sensor and second characteristics dependent upon the undesirable properties of the incident light signal;
   detection means responsive to the reflective light signal for detecting the first characteristics of the reflective light signal to provide an indication of the physical parameter in the environment; and
   a filter included in the detection means and disposed in the particular environment, the filter having optical properties which inhibit the second characteristics of the reflected light signal.

2. The apparatus recited in claim 1 further comprising:
   means for providing the source of light an optical spectrum which moves in a particular direction in response to the change in temperature; and
   means for providing the filter with an optical spectrum which moves in the particular direction in response to the change in temperature.

3. A catheter assembly adapted for measurement of a fluid pressure within a body cavity of a patient, comprising:
   a light source having a temperature providing an optical signal having thermal drift characteristics which vary in response to a change in the temperature of the light source;
   optical sensor means adapted to receive the optical signal from the light source to provide a measurement signal indicative of the fluid pressure in the cavity, the measurement signal having undesirable characteristics related to the thermal drift characteristics of the light source;
   detection means coupled to the optical sensor means for detecting the measurement signal to provide an output signal indicative of the fluid pressure in the cavity;
   a filter included in the detection means and having optical characteristics which substantially offset the undesirable characteristics of the measurement signal; whereby
   the output signal is substantially independent of the temperature of the light source.

4. The assembly recited in claim 3 wherein:
   each of the light source and the filter has a spectrum;
   the output signal is dependent upon the area of a spectral envelope defined on one side by the spectrum of the light source and defined on the other side by the spectrum of the filter; and the assembly further comprises:
   means for causing the spectrum of the light source to shift in a particular direction in response to the change in temperature; and
   means for causing the spectrum of the filter to shift in the particular direction in response to the change in temperature.

5. The assembly recited in claim 3 wherein each of the light source and the filter has a spectrum and the assembly further comprises:
   means included in the light source and responsive to a change in temperature of the light source for causing the spectrum of the light source to drift in a particular direction; and means included in the filter and responsive to a change in temperature of the filter for causing the spectrum of the filter to drift in the particular direction to about the same extend as the drift of the light source.

6. The assembly as set forth in claim 3 wherein each of the light source and the filter has a spectral frequency curve, and the assembly further comprises:
means providing the output signal with characteristics responsive to variations in a particular area beneath an envelope defined by the spectral frequency curve of the light source and the spectral frequency curve of the filter; and
means responsive to an increase in temperature, for causing the particular area of the envelope to decrease with a shift in the spectral frequency curve of the light source and to increase with a shift in the spectral frequency curve of the filter.

7. The assembly recited in claim 6 wherein the particular area of the envelope is defined in one direction by the spectral frequency curve of the filter and in another direction by the spectral frequency curve of the light source, and the assembly further comprise:
means responsive to an increase in temperature for moving the spectral frequency curve of the light source in the one direction to increase the particular area;
means responsive to the increase in temperature for moving the spectral frequency curve of the filter in the one direction to decrease the particular area of the envelope; whereby
the size of the particular area remains substantially constant in response to the increase in temperature.

8. A catheter assembly adapted for measurement of a fluid pressure within a body cavity of a patient, comprising:
an electrical power source;
optical conversion means responsive to the electrical power source for providing an optical signal;
a light emitting diode included in the optical conversion means and having a spectrum, the diode having thermal drift characteristics which vary in response to a change in temperature such that the spectrum of the diode shifts to longer wavelengths in response to an increase in temperature;
optical sensor means adapted to receive the optical signal from the optical conversion means and to provide a measurement signal indicative of the fluid pressure in the cavity, the measurement signal having undesirable characteristics related to the thermal drift characteristics of the diode;
detection means coupled to the optical sensor means for detecting the measurement signal to provide an output signal indicative of the fluid pressure in the cavity;
a filter included in the detection means and having a spectrum, the filter having optical characteristics such that the spectrum of the filer shifts to longer wavelengths in response to an increase in temperature;
the output signal is dependent upon the area of the spectral envelope which is defined on one side by the spectrum of the diode and which is defined on the other side by the spectrum of the filter; whereby
the area beneath the envelope is substantially unchanged in response to an increase in temperature.

9. A catheter assembly for measuring a fluid pressure within a body cavity of a patient, comprising:
a catheter having a distal end adapted for disposition in the body cavity of the patient;
optical pressure sensor means coupled to the catheter, the sensor means having a temperature and properties for providing an optical measurement signal indicative of the fluid pressure in the body cavity;
detection means responsive to the optical measurement signal for providing an electrical signal indicative of fluid pressure in the body cavity;
the optical measurement signal including undesirable optical components which vary with the temperature of the sensor means and provide the optical measurement signal with a signal-to-noise ratio; and
filter means included in the detection means for inhibiting the undesirable optical components of the optical signal which vary with the temperature of the sensor means in order to increase the signal-to-noise ratio of the optical measurement signal.

10. The catheter assembly recited in claim 9, wherein:
the optical measurement signal is a first optical signal having a first signal-to-noise ratio; and
the filter means provides a corrected optical signal having a second signal-to-noise ratio higher than the first signal-to-noise ratio.

11. The catheter assembly recited in claim 10, wherein:
the first optical signal has a spectrum with variations responsive to temperature; and
the filter means includes an optical filter having a spectrum which reduces the variations in the spectrum of the first optical signal in order to increase the signal-to-noise of the corrected optical signal.

12. The catheter assembly recited in claim 9 wherein the optical pressure sensor means comprises:
a light source providing an optical signal having characteristics which vary in response to the temperature of the sensor means; and
a sensor responsive to the optical signal of the light source to provide the optical pressure measurement signal indicative of the fluid pressure in the body cavity.

13. The catheter assembly recited in claim 12 wherein:
the light source is disposed in a particular environment which establishes the temperature of the light source; and
the filter means is disposed in the particular environment which establishes the temperature of the filter means, the filter means having properties for inhibiting the undesirable optical components of the optical signal which vary with the temperature of the light source in order to increase the signal-to-noise ratio of the optical measurement signal.

14. A catheter assembly for measuring a fluid pressure within a body cavity of a patient, comprising:
a catheter having a distal end adapted for disposition in the body cavity of the patient;
a light source disposed in a particular environment that establishes the temperature of the light source, the light source providing an optical signal having characteristics which vary in response to a change in the temperature of the light source;
an optical pressure sensor disposed generally at the distal end of the catheter and responsive to the optical signal of the light source to provide an optical measurement signal indicative of the fluid pressure in the body cavity;

detection means responsive to the optical measurement signal for providing an electrical signal indicative of fluid pressure in the body cavity;

the optical measurement signal including undesirable optical components which vary with the temperature of the light source and provide the optical measurement signal with a signal-to-noise ratio; and filter means includes in the detection means and disposed in the particular environment that establishes the temperature of the filter means, the filter means having properties for inhibiting the undesirable optical components of the optical signal which vary with the temperature of the light source in order to increase the signal-o-noise ratio of the optical measurement signal.

15. A catheter assembly for measuring a fluid pressure within a body cavity of a patient, comprising;

a catheter having a distal end adapted for disposition in the body cavity of a patient;

optical pressure sensor coupled to the catheter, the sensor means having a temperature and properties for providing an optical measurement signal indicative of the fluid pressure in the body cavity;

detection means responsive to the optical measurement signal for providing an electrical signal indicative of fluid pressure in the body cavity;

the optical measurement signal including undesirable components which vary with the temperature of the sensor means;

means included in the detection means for compensating for the undesirable components of the optical signal which vary with the temperature;

first amplifier means included in the detection means and responsive to the optical measurement signal for providing the electrical signal with first components representative of the optical measurement signal including the undesirable components;

means included in the compensation means for filtering the optical signal to provide a corrected signal adjusted in accordance with the undesirable components of the optical signal;

second amplifier means included in the detection means and responsive to the corrected means for providing the electrical signal with second components representative of the optical measurement signal excluding the undesirable components;

conversion means coupled to the detection means for providing a digital signal indicative of the fluid pressure in the body cavity; and output means responsive to the digital signal for displaying the fluid pressure in the body cavity.

16. The assembly defined in claim 15 further comprising:

memory means responsive to the digital signal of the conversion means for storing a particular digital quantity representative of the value of the digital signal when the fluid pressure in the body cavity is zero; and the output means being responsive to the particular digital value stored in the memory means to provide an analog signal indicative of a zero pressure in the body cavity.

17. The assembly recited in claim 15 wherein the conversion means includes divider means coupled to the first and second amplifiers for providing the digital signal with characteristics indicative of the first components of the electrical signal divided by the second components of the electrical signal.

18. A catheter assembly for measuring a fluid pressure within a body cavity of a patient, comprising:

a catheter having a distal end adapted for disposition in the body cavity of a patient;

a light source disposed in a particular environment that establishes the temperature of the light source, the light source providing an optical signal having characteristics which vary in response to a change in the temperature of the light source;

an optical pressure sensor disposed generally at the distal end of the catheter and responsive to the optical signal of the light source to provide an optical measurement signal indicative of the fluid pressure in the body cavity;

detection means responsive to the optical measurement signal for providing an electrical signal indicative of fluid pressure in the body cavity;

the optical measurement signal including undesirable components which vary with the temperature of the light source;

compensating means included in the detection means and disposed in the particular environment that establishes the temperature of the compensating means, the compensating means having properties for compensating for the undesirable components of the optical signal which vary with the temperature of the light source;

first amplifier means included in the detection means and responsive to the optical measurement signal for providing the optical measurement signal including the undesirable components;

means included in the compensating means for filtering the optical signal to provide a corrected signal adjusted in accordance with the undesirable components of the optical signal;

second amplifier means included in the detection means and responsive to the corrected signal for providing the electrical signal with second components representative of the optical measurement signal excluding the undesirable components;

conversion means coupled to the detection means for providing a distal signal indicative of the fluid pressure in the body cavity; and output means responsive to the digital signal for displaying the fluid pressure in the body cavity.

19. A method for reducing the effect of a change in temperature on an optical system including a sensor having properties dependent upon a change in pressure, the method comprising the steps of:

directing an incident light signal onto the sensor, the incident light signal having undesirable properties dependent upon the change in temperature;

sensing the change in pressure;

receiving a reflective light signal from the sensor, the reflective light signal having first characteristics dependent upon the change in pressure sensed by the sensor, and second characteristics dependent upon the change in temperature;

directing the reflective light signal through an optical filter to inhibit the second characteristics in the reflective light signal; and detecting the first characteristics in the reflective light signal to provide an indication of the pressure sensed by the sensor.

20. The method recited in claim 19 wherein during the inhibiting step the method further comprising the steps of:

increasing the area of the combination spectrum in response to the change in temperature, the area of the combination spectrum being defined on one side by a first spectrum dependent upon the undesirable properties of the incident light signal, and defined on the other side by a second spectrum which varies in response to the change in temperature; and decreasing the area of the combination spectrum in response to variations in the second spectrum in response to the change in temperature.

21. The method recited in claim 19 wherein during the inhibiting step the method further comprises the steps of:

providing a combination spectrum with an area defined on one side by a first spectrum dependent on the undesirable properties of the incident light signal, and defined ion another side by a second spectrum which varies in response to the change in temperature;

increasing the area of the combination spectrum in response to variations of the first spectrum resulting from the change in temperature; and decreasing the area of the combination spectrum in response to the variations of the second spectrum resulting from the change in temperature.

* * * * *